United States Patent [19]

Abell et al.

[11] Patent Number: 6,106,506

[45] Date of Patent: Aug. 22, 2000

[54] METHOD AND APPARATUS FOR DELIVERING A COLONIC LAVAGE

[75] Inventors: Roy Abell, Duluth; Kenneth E. Hill, Monroe, both of Ga.; Paul J. Mann, Huntsville, Ala.

[73] Assignee: Innovatec Medical Corp., Norcross, Ga.

[21] Appl. No.: 09/031,225

[22] Filed: Feb. 26, 1998

Related U.S. Application Data

[63] Continuation-in-part of application No. 08/811,816, Mar. 4, 1997.

[51] Int. Cl.⁷ .............................. A61M 31/00; A61M 1/00
[52] U.S. Cl. ......................... 604/275; 604/257; 604/259; 604/261; 604/28; 604/30
[58] Field of Search ................................ 604/27–36, 39, 604/41, 43, 523, 514, 275–278, 257–61

[56] References Cited

U.S. PATENT DOCUMENTS

| | | | |
|---|---|---|---|
| 1,696,018 | 12/1928 | Schellberg | 604/523 |
| 2,022,742 | 12/1935 | Salerni | 604/118 |
| 2,074,374 | 3/1937 | Suarez de Mendoza | 604/259 |
| 2,257,072 | 9/1941 | Coombs | 604/259 |
| 2,458,719 | 1/1949 | McCormick | 604/275 |
| 2,873,739 | 2/1959 | Whann | 604/275 |
| 2,874,696 | 2/1959 | Bried | 604/275 |
| 3,042,044 | 7/1962 | Sheridan | 128/348 |
| 3,678,932 | 7/1972 | Hudson | 604/259 |
| 3,771,522 | 11/1973 | Waysilk et al. | 128/227 |
| 3,823,714 | 7/1974 | Waysilk et al. | 128/229 |
| 4,332,246 | 6/1982 | Thomson | 128/214 |
| 4,403,982 | 9/1983 | Clayton | 604/28 |
| 4,626,239 | 12/1986 | Ardizzone | 604/259 |
| 4,637,814 | 1/1987 | Lieboff | 604/27 |
| 4,842,580 | 6/1989 | Oulette | 604/275 |
| 4,874,363 | 10/1989 | Abell | 604/28 |
| 5,019,056 | 5/1991 | Lee et al. | 604/48 |
| 5,176,630 | 1/1993 | Shilling et al. | 604/41 |
| 5,190,519 | 3/1993 | Mead et al. | 604/27 |
| 5,197,947 | 3/1993 | Harris | 604/28 |
| 5,405,319 | 4/1995 | Abell et al. | 604/27 |
| 5,496,269 | 3/1996 | Snoke | 604/28 |
| 5,788,650 | 8/1998 | Dotolo | 600/562 |
| 5,871,463 | 2/1999 | Baker et al. | 604/27 |

FOREIGN PATENT DOCUMENTS

| | | | |
|---|---|---|---|
| WO 87/01596 | 3/1987 | WIPO | A61M 1/00 |
| WO 88/00840 | 2/1988 | WIPO | A61M 1/00 |

*Primary Examiner*—Corrine McDermott
*Assistant Examiner*—Patricia M Bianco
*Attorney, Agent, or Firm*—Womble Carlyle Sandridge & Rice

[57] ABSTRACT

A portable apparatus (51) for delivering a colonic lavage to a patient includes a portable frame (52) preferably constructed of tubing, a lavage liquid reservoir (71) and a waste reservoir (72) both stowable in the frame (52), a speculum (78) for delivering the lavage liquid to the interior of a colon and for receiving waste from the colon, a waste conduit (88) communicating at one end with the speculum (78) and at another end with the waste reservoir (72), and a first sphincter valve (87) selectively opening and closing the waste conduit (88). A pump (66) housed in the frame (52) delivers the lavage liquid from an interior cavity of the frame (52) to the speculum (78) via a delivery conduit (91) coupling the speculum (78) with a pump tube (102) communicating with the pump (66). A regulator valve assembly (58) communicates with the pump tube (102) and ensures that the lavage liquid is never delivered to the colon above a predetermined pressure. A second sphincter valve (92) selectively opens and closes the delivery conduit (91) responsive to a controller (64), which may operate according to a predetermined schedule to deliver a pulsed supply of lavage liquid to the colon for dislodging impacted fecal material therefrom. The controller (64), operatively connected to both the first sphincter valve (87) and the second sphincter valve (92), effects the closing of waste conduit (88) during delivery of the lavage liquid, as well as the closing of the delivery conduit (91) during removal of waste from the colon.

42 Claims, 5 Drawing Sheets

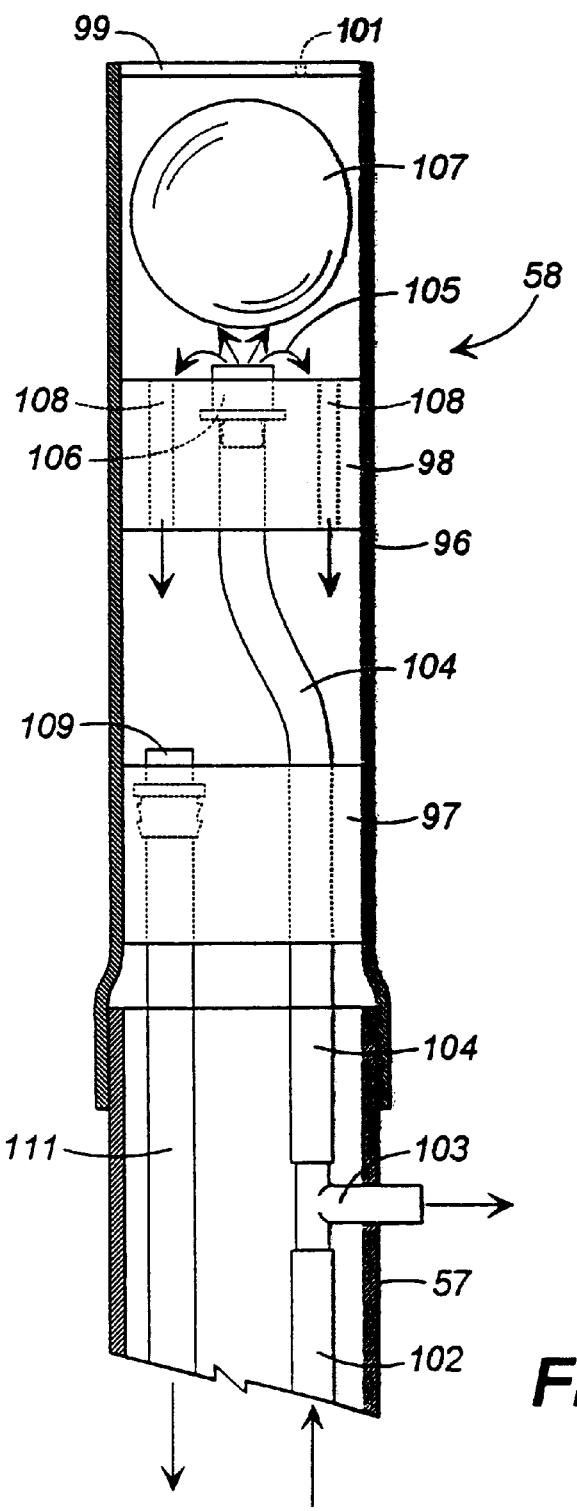
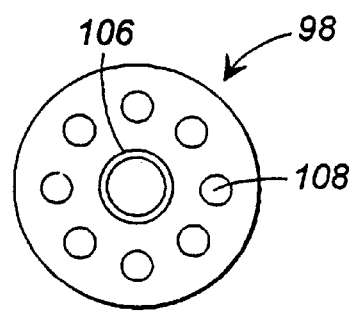
FIG. 6
FIG. 5

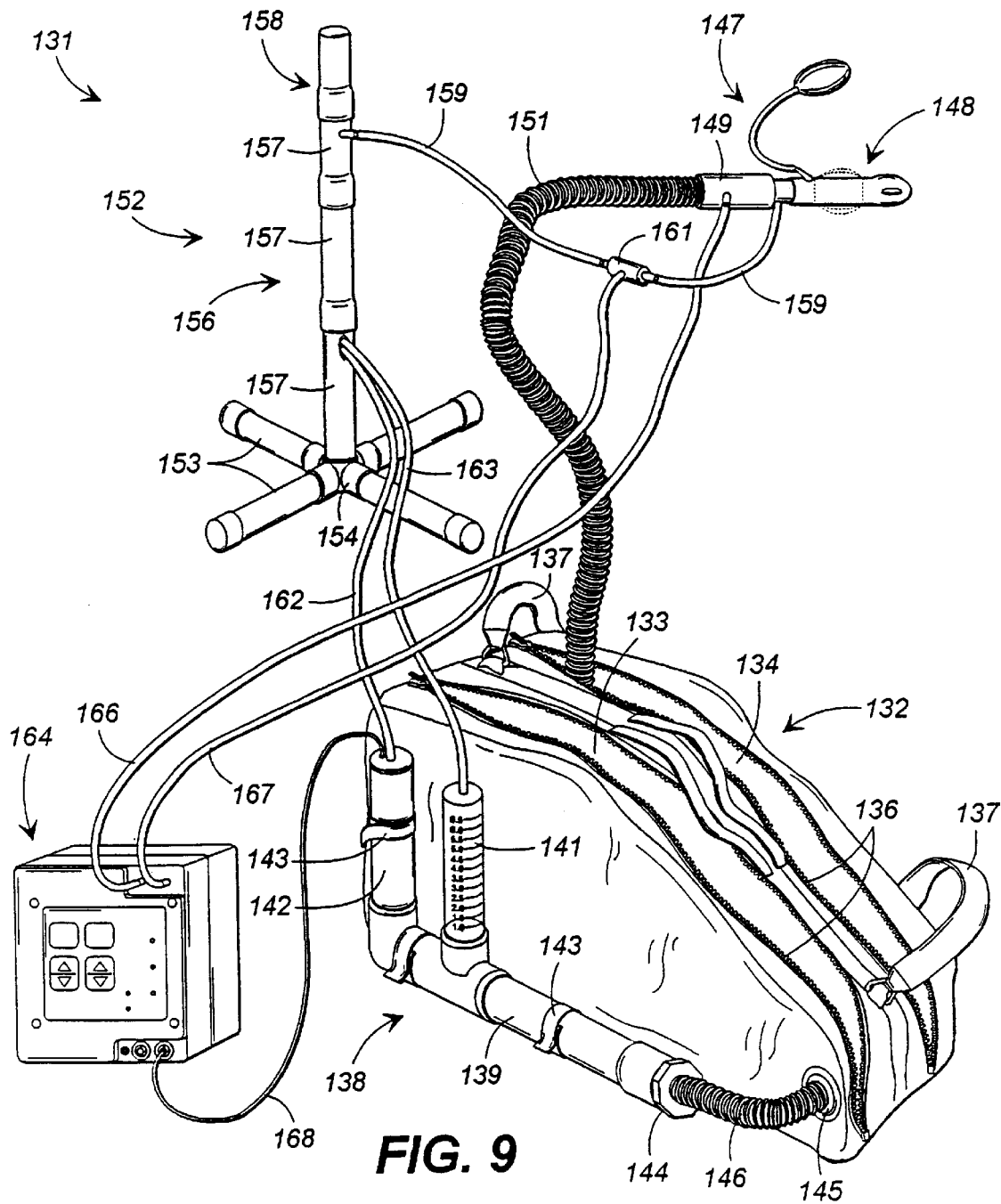
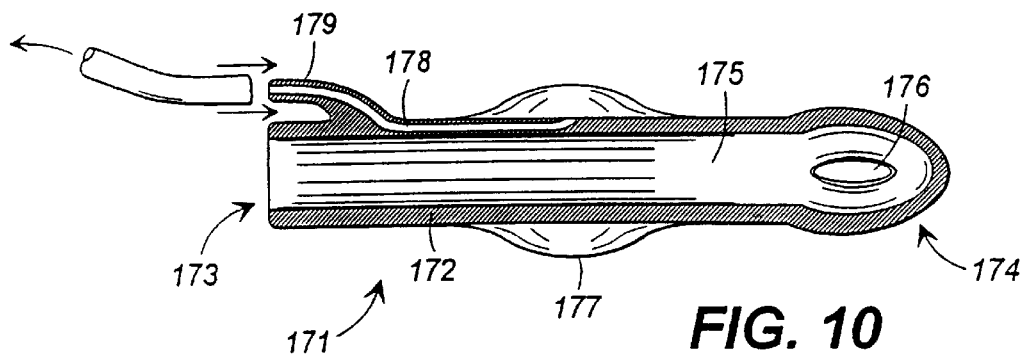

METHOD AND APPARATUS FOR DELIVERING A COLONIC LAVAGE

REFERENCE TO RELATED APPLICATION

This application is a continuation-in-part of pending U.S. patent application Ser. No. 08/811,816 filed Mar. 4, 1997.

TECHNICAL FIELD

This invention relates generally to devices and methods of delivering a colonic lavage and to pneumatically or hydraulically controllable sphincter valves usable in such devices and methods.

BACKGROUND OF THE INVENTION

In a variety of medical applications, valves are used to control the inflow and outflow of fluids into and out of a patient's body. Such applications include, among others, blood transfusions, stomach evacuations, heart lung machine procedures, and colonic lavage for the removal of fecal impactions from a patient's bowels and removal of fecal material during normal bowel maintenance programs. In the case of colonic lavage, it is common that a first valve is connected in the liquid supply line of the lavage apparatus to control the inflow of water or other lavage liquid into a patient's colon for hydrating and loosening dry impacted fecal material. A second valve is connected in the drain line. This first valve is closed and the second valve usually is closed during fluid inflow to allow the bowels of the patient to fill with fluid. The second valve can then be opened to allow fluid and loosened fecal material to flow out of the patient's colon to an appropriate receptacle.

Valves used in colonic lavage systems and, indeed, in other medical applications, are subject to a number of relatively severe operational constraints. First, such valves must be extremely reliable because the lives of patients can and often are dependent upon their flawless operation. In addition, the valves must be gentle in that they must open and close in such a way that fluid flow is not stopped or started abruptly, which can shock a patient's system or damage delicate tissues. This is particularly true in the case of colonic lavage procedures because colon walls are thin and subject to rupture under abrupt stresses. It is also important in colonic lavage procedures that valves used in the system have the ability to cause a relatively rapid pulsing of the lavage inflow liquid during the inflow cycle to create a wave activity in the water or other lavage liquid to aid in the loosening of fecal impactions. In addition, such valves must be opened reliably and automatically in response to excess back pressure from the colon in order to prevent damage to the colon as a result of excess fluid pressure being created in the colon by colon muscle contractions.

In the past, a variety of valves have been used in medical procedures such as those discussed above. In many cases, a sphincter valve design has been adopted because of its many advantages. In a sphincter valve, communication through the valve is closed by squeezing or collapsing a flexible tube within the valve through which the fluid passes. The valve is opened by releasing the flexible tube to allow the fluid to flow. This squeezing and releasing has been accomplished in a number of ways. In a heart lung machine, for example, the tube is squeezed and released by moving rollers that intermittently engage, compress, and roll along a short length of the tube. This action not only closes the valve, it also has the effect of pumping fluid intermittently through the tubing. In another type of sphincter valve, a mechanical plunger is actuated to engage and compress the flexible tube to close off communication therethrough.

One sphincter valve design that has proved itself reliable is the pneumatically controlled sphincter valve. Such valves have proven particularly useful in colonic lavage systems. In these types of valves, a short, flexible, collapsible tube is enclosed within a pressure chamber coupled to a source of selectively applyable compressed air. The tube is coupled or spliced into the lavage liquid delivery line to control lavage fluid inflow. A similar valve may be spliced into the waste drain line to control the flow of contaminated fluid from the patient's colon. When it is desired to close one of the valves, pressurized air is injected into the pressure chamber. This generates inward force that collapses the interior tube and shuts off the flow therethrough.

In the past, pneumatic sphincter valves have been constructed of a hard injection molded plastic outer shell having corresponding injection molded end caps that can be glued in place to form a generally cylindrical pressure chamber. A short tubular nipple communicates with the interior of the chamber and projects outwardly from the side thereof for selective delivery of pressurized air to the pressure chamber. Each of the end caps is molded with a short tubular coupler that extends and communicates through the end cap and that has an interior end within the chamber and an exterior end outside the chamber. A length of flexible surgical tubing is secured at its ends to the interior ends of the couplers communicating therebetween. The entire assembly is spliced into a liquid delivery or drain line by cutting the line if necessary and coupling the cut ends of the line to the exterior portions of the tubular couplers. Thus, fluid can flow from one section of the line, through the flexible tube within the chamber, and into the other section of the line. The tubular nipple is coupled to a source of selectively deliverable compressed air. When it is desired to shut the valve off, compressed air is injected into the pressure chamber, exerting pressure on the flexible tube within to compress and collapse the tube, thus shutting off the flow. For opening the valve, the pressure is simply released.

While the just described pneumatic sphincter valve design has proved useful and reliable, it nevertheless embodies certain problems and shortcomings inherent in its design. For example, the valve is relatively expensive to manufacture because key components are injection molded. Further, the valve is time consuming and thus expensive to fabricate because the internal flexible tube must be installed manually and the end caps and other components must be glued to the chamber by hand. The hard plastic shell of the chamber can shatter if dropped and is uncomfortable to the skin of a patient such that the valve cannot comfortably be laid or rested on the patient during use. Finally, since the flexible internal tube of the valve is separate and made of a different material than other valve components, it can, under certain circumstances, come loose from the couplers within the valve causing the valve to fail and risking contamination of the compressed air supply.

For these reasons, and particularly due to the expense of production and fabrication, conventional pneumatic sphincter valves have not been economical for use with disposable colonic lavage kits designed to be discarded after a single use. Accordingly, such disposable kits have been expensive and thus not easily available to lower income persons or patients on fixed incomes.

Prior art devices have also been available for delivering a colonic lavage to a patient in order to dislodge and remove fecal material from the patient's colon. Some examples of such devices are disclosed in U.S. Pat. No. 5,190,519 of Mead et al., 5,176,630 of Shilling, et al., 5,405,319 of Abell et al., 5,019,056 of Lee et al., and 4,874,363 of Abell. Each of these devices has as its primary purpose the delivery of a lavage liquid into the colon of a patient for dislodging fecal material that may be lodged therein and then removing or draining the dislodged material along with the waste lavage liquid from the colon to evacuate the bowels of the patient. Each of these devices may be used to accomplish this task. However, the devices of these patents are also burdened with various problems and shortcomings inherent in their various designs. For example, the Lee et al. device is large, bulky, and heavy and is suited for use only by medical personnel in the confines of a doctor's office, hospital, or other appropriate facility. It is not suitable for personal use by a patient in his or her home and certainly can not be carried easily on vacations and trips for use away from home. In addition, the pumping and valving mechanisms of this device tend to deliver lavage liquid to the colon in a harsh manner that can be uncomfortable for the patient and ineffective in removing certain types of fecal impactions. Also, the valves and speculum disclosed by Lee et al. are formed of hard components that can be uncomfortable and that include injection molded plastic parts, which are relatively expensive, especially for single use disposable items.

Shilling et al. discloses a combination speculum and sphincter valve assembly that, again, is formed of hard plastic injected molded components that are expensive to manufacture and uncomfortable to use.

Abell et al. discloses a manually controlled bowel evacuation system that, while somewhat portable, nevertheless falls short of an ideal system. This device includes a speculum for insertion into the rectum, a source of pressurized water connected to the speculum, and a drain hose connected to the speculum for draining waste material to a waste receptacle. A squeeze bulb is coupled to actuate a pair of valves that alternately close off the drain hose while delivering water to the speculum and opening up the drain hose while closing off the pressurized water hose. In this way, it is taught, fecal material is dislodged by water flowing into the colon and drained when the drain hose is opened. The problems with the device lie in its complex valving mechanisms that are both expensive to manufacture. In addition, the device is strictly manually operated and therefore the benefits of the rapid pulsing wave activity in the water, controlled by the system of electronics, are not achievable. Also, a variety of modes of valve operation for controlling the inflow of water and the outflow of waste are not possible because of the limited design of the valving system.

Finally, Abell discloses a colon hydrotherapy and evacuator system that includes a water reservoir, a pump for delivering water from the reservoir to a colon through a speculum, and a drain line for delivering dislodged waste from the colon to a separate receptacle for disposal. A single mechanical ball-type valve is provided in the drain line. In use, water is pumped continuously to the colon and the drain valve is periodically opened and closed to allow water to accumulate in the colon and then to drain the accumulated water to the waste receptacle. Clearly, this device lacks intelligent control functions and represents a "brute force" method of evacuating a colon. Further, it is not easily portable, has mechanical valves and pumps that are expensive and somewhat less than perfectly reliable, and is not capable of controlled cycled operation in a variety of modes.

There is thus a need for a lightweight, self contained, reliable, automatically controlled, integrated apparatus for delivering a colonic lavage that overcomes the problems of the prior art. The apparatus should be easily transported, be made with highly reliable yet economical valves, speculums, and receptacles that can be used once and thrown away. There is a further need for a reliable, unbreakable, and economical sphincter valve that can be used with colonic lavage and other medical procedures and discarded after use. It is to the provision of such an apparatus and sphincter valve that the present invention is primarily directed.

SUMMARY OF THE INVENTION

Briefly described, the present invention, in one preferred embodiment thereof, comprises a unitary sphincter valve assembly intended primarily for use in medical applications such as colonic lavage procedures. The valve assembly preferably is molded in a single molding step from a translucent, opaque, or pigmented pliant silicone material. The completed assembly is formed from two parts, a main body and an end cap, each of which can be molded of a unitary mold. The main body of the assembly is formed to define a generally cylindrical relatively thick walled outer shell and a relatively thin walled interior tube that extends coaxially within the outer shell and that has a central passageway. A pressure chamber is defined between the outer shell and the interior tube and the central passageway continues and communicates through the end of the main body where a female coupling nipple provides a means for coupling the valve in a fluid delivery line. The outer shell of the main body is formed with a tubular coupling nipple that projects outwardly from the wall of the outer shell and communicates with the pressure chamber between the outer shell and the interior tube.

Molded simultaneously with and of the same silicone material as the main body is an end cap that, in use, is inserted in the other end of the main body to form the completed valve assembly. The end cap has a central passageway, an inwardly projecting plug, a shoulder or flange, and an outwardly projecting female coupling nipple similar to the coupling nipple formed on the opposite end of the main body of the valve. When installed in the end of the main body, the plug is sealingly received within the end of the interior tube so that the tube passageway is continued through the end cap and through the coupling nipple to define a continuous passageway through the valve. The shoulder or flange of the valve abuts and is sealed about the end of the outer shell of the main body to close off the pressure chamber defined between the outer shell and the interior tube.

In use, the valve assembly of this invention functions in much the same way as prior art sphincter valves. Specifically, the valve is spliced in a fluid flow line by coupling one section of the line to the coupling nipple on one end of the valve and coupling the other section of the line to the coupling nipple on the opposite end of the valve. Thus, fluid is free to flow through the central passageway of the valve. An air pressure supply tube is coupled to the coupling nipple projecting from the main body for selective delivery of pressurized air to the pressure chamber.

With no pressurized air supplied to the pressure chamber, fluid is free to flow through the valve unimpeded. In this condition, the valve is open. When it is desired to close the valve, pressurized air is supplied to the pressure chamber. As the air enters the chamber, it exerts inward force on the interior tube causing it to collapse on itself closing off communication through the valve and shutting off the flow of fluid. Thus, the valve can be opened and closed by selectively supplying pressurized air to and releasing the pressure from the pressure chamber of the valve. In practice, the valve can be cycled in this way up to several times per second if desired.

It has been found that the valve of this invention, in addition simply to opening and closing, provides an added function that is particularly beneficial in colonic lavage applications. Specifically, as pressurized air is supplied to the pressure chamber, the interior tube first collapses at its center and continues to collapse toward the ends of the valve as it closes. This acts to squeeze the fluid within the passageway out of the valve causing a short pulse of fluid through the fluid flow line. When the valve is cycled rapidly, the result is a pulsating flow of fluid resulting in a gentle wave activity in the lavage fluid, which, when the valve is used in the fluid supply line of a colonic lavage apparatus, acts to loosen and dislodge impacted fecal material in a patient's colon. While this pulsing function also occurs with prior art hard shell sphincter valves, it has been found that the flexibility of the unitary silicone structure of the present invention provides pulsing action superior to that of prior art valves.

Another aspect of the present invention comprises a greatly improved apparatus and method for delivering a colonic lavage to a patient. In one embodiment, the apparatus includes a frame constructed of substantially hollow tubular elements connected together to form a sealed interior cavity for containing a lavage liquid. The frame thus functions both as a support structure and as a reservoir for lavage liquid. The frame is configured to carry a supplemental lavage liquid reservoir in the form of a plastic bag and waste receptacle, also in the form of a plastic bag, for receiving waste material from a patient's colon for disposal and is supported on wheels for easy mobility. A speculum is provided that, preferably, is unitarily molded of a rubberized material such as silicone, and is configured to be inserted into a patient's colon for delivering lavage liquid to the colon and draining waste liquid from the colon. A pump is disposed in the hollow frame for pumping lavage liquid through a tube to the speculum and a waste tube couples the speculum to the waste receptacle. A gravity actuated ball and seat regulator valve located atop a pylon of the frame is coupled to the supply tube to insure that the pressure of lavage liquid delivered to the patient does not exceed a predetermined threshold.

A pair of sphincter valves, preferably formed according to the present invention as summarized above, are disposed in line with the lavage liquid supply tube and the waste removal tube respectively. A programmable computer-based controller is coupled to the pump and to each of the sphincter valves and can control each of these elements individually or in any desired phased relationship relative to each other. In use, the controller selectively actuates the pump and the sphincter valves according to a predetermined cycled schedule to provide a gentle pulsed supply of lavage liquid to the colon for dislodging fecal material therein and, at the appropriate time, draining the resulting waste liquid from the colon to the receptacle carried by the frame. Both valves can be closed simultaneously if desired to hold the liquid in the colon for improved hydration of stool performance. A variety of other operational modes are available, including a manual mode, to provide the most effective colon evacuation under a variety of circumstances.

In another embodiment of the invention, the colonic lavage device is configured as a portable carryable unit. All of the basic elements of the device are contained in a cloth carrier about the size of a suitcase that can be carried over a shoulder and packed in a vehicle for travel. In this way, the colonic lavage apparatus of this invention can easily be carried with a patient on trips for providing a colonic lavage whenever needed. This provides a mobility and freedom heretofore not possible for patients requiring frequent bowel evacuation.

The colonic lavage apparatus of this invention provides a variety of advantages over prior art devices. First, it is lightweight, easily portable, and relatively inexpensive to manufacture, making it affordable to an average patient for in-home use. The doubling of the hollow frame as both a support structure and a lavage liquid reservoir increases the efficiency of the device and provides ease of use. The unitary molded valves and speculum are much less expensive than constructions of the prior art and can be included in a kit of disposable elements that are discarded after a single use.

Thus, it is an object of this invention to provide a sphincter valve that is inexpensive to manufacture relative to prior art valves but that functions as well or better.

Another object of the invention is to provide a sphincter valve that is reliable yet economical enough to be discardable after a single use.

A further object of the invention is to provide a sphincter valve that can be assembled quickly and with minimum labor.

A still further object of the invention is to provide a sphincter valve having a soft body that is not uncomfortable to the skin of a patient so that it can be laid or rested on a patient's body during use if desired.

An additional object of the invention is to provide a lightweight, portable, easy to use colonic lavage apparatus that can be carried to and/or used by a patient in his home rather that requiring the patient to travel to a medical facility to receive a colonic lavage.

Another object of the invention is to provide an improved method of delivering a colonic lavage that is reliable, repeatable, and easily applied to a patient in his or her home.

These and other objects, features, and advantages of the present invention will become apparent upon review of the detailed description set forth below when taken in conjunction with the accompanying drawings, which are briefly described as follows.

BRIEF DESCRIPTION OF THE DRAWINGS

FIG. 5 is a cross-sectional view of the gravity actuated regulator valve assembly of the present invention.

FIG. 6 is a top plan view of the regulator valve stopper showing return holes formed therein.

FIG. 9 is a perspective view of the present invention embodied in a portable carryable kit for taking on trips.

FIG. 10 is a side elevational cross-sectioned view of a unitarily molded rubberized speculum that embodies principles of the present invention.

DETAILED DESCRIPTION OF THE PREFERRED EMBODIMENT

Figure 1:
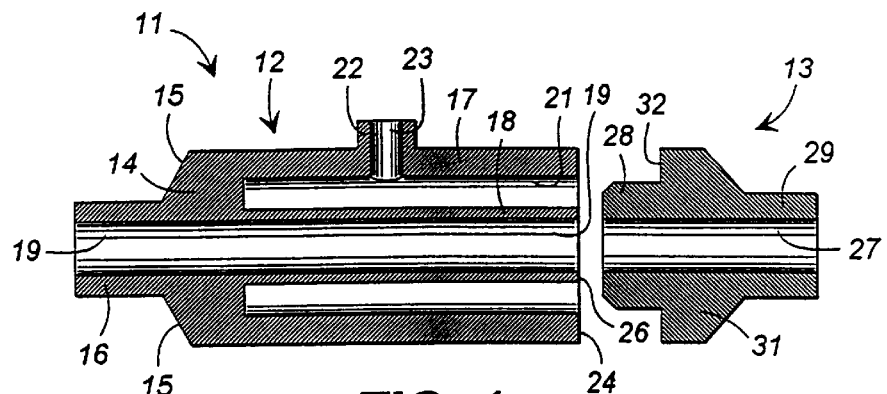
FIG. 1 is a side cross-sectional view of a unitary sphincter valve assembly for use in a colonic lavage apparatus that embodies principles of the present invention in a preferred form.

Referring now to the drawings, wherein like numerals refer to like parts throughout the several views, FIG. 1 illustrates in cross-section a sphincter valve assembly that embodies principles of the present invention in a preferred form. The sphincter valve assembly of FIGS. 1 through 4 are particularly suitable for use in the colonic lavage method and apparatus of this invention. The assembly 11 comprises two components, a main body 12 and an end cap 13. Both the main body 12 and the end cap 13 preferably are molded at the same time and in a common mold. Further, both components in the preferred embodiment are formed of a flexible somewhat rubber like material such as, for example, a silicone, a silicone rubber compound, or another synthetic rubber material. Latex materials can also be used, but they are not preferred for applications where the valve is likely to come into contact with a patient's skin because many patients have latex allergies. In any event, the material can be uncolored or pigmented if desired and preferably is translucent or partially transparent so that a user can observe the operation of and fluid flow through the valve.

The main body 12 is formed to define a generally cylindrical outer shell 17 that surrounds and is coaxially aligned with a smaller interior tube 18. The outer shell 17 is molded to have relatively thick walls so that it is substantially rigid, although some flexibility is provided in the outer shell because of the flexible nature of the silicone material from which it is molded. Conversely, the walls of the interior tube are relatively thin compared to those of the outer shell so that the interior tube is flexible and can be collapsed upon itself under the influence of appropriate inward force applied to the outside of the tube. The interior tube 18 is spaced from the inner walls of the outer shell 17 so that an annular or cylindrical pressure chamber 21 is defined between the outer shell and the interior tube.

The main body 12 is also formed with an end portion 14 that is integrally molded with the outer shell and the interior tube and from which they extend. The end portion 14 is molded with a shoulder 15 from which a female coupling nipple 16 axially extends. The end portion closes off the pressure chamber at the end of the valve and supports the end of the interior tube 18 relative to the outer shell 17. The central passageway 19 of the interior tube 18 extends continuously through the end portion 14 of the main body and axially through the coupling nipple 16 to define a continuous uninterrupted passage through the valve. At the other end of the main body 12, the outer shell 17 terminates in an end 24 and the interior tube 18 terminates in an end 26. In the preferred embodiment, the ends 24 and 26 and substantially coplanar; however, this is not a requirement and one of the ends could well be recessed with respect to the other end.

The end cap 13 is formed with a central axially extending passageway 27 that preferably has the same diameter as the central passageway 19 defined through the main body 12. The end cap 13 is also formed with a radially extending flange 31, an inwardly extending plug 28, and an outwardly extending coupling nipple 29. The flange 31 defines a shoulder 32 that is sized and configured to abut the end 24 of the outer shell 17 when the end cap 13 is installed in the end of the main body as described in more detail below.

The outside diameter of the inwardly extending plug 28 is larger than the inside diameter of the central passageway 19 of the interior tube and preferably is substantially the same as the inner diameter of the pressure chamber 21. With this configuration, the end 26 of the interior tube 18 and the end 24 of the pressure chamber can be stretched to a larger diameter with an appropriate stretching tool and the inwardly extending plug 28 can be inserted into the stretched ends as the end cap is installed. When the stretched ends are released, they tend to return to their original size thereby closing and sealing around the outside of the plug 28. More specifically, the end 24 of the pressure chamber, when released, closes around the plug 28 and around the tube 18 capturing the end 26 of the tube between the plug and the interior wall of the pressure chamber. This securely fixes the end of the tube and forms a continuous sealed passageway completely through the valve from the left coupling nipple 16, through the interior tube 18, and out the right coupling nipple 29. It is also preferable when installing the end cap that a bead of silicone adhesive be applied between the end 24 of the outer shell 17 and the shoulder 32 of the end cap. In this way, the pressure chamber 21 is reliably sealed against any leakage between the end of the main body 12 and the end cap 13.

A female coupling nipple 22 projects radially outwardly from the outer shell 17 and has a central passageway 23 that communicates with the pressure chamber 21. As described below, the nipple 22 is adapted to be coupled to a pressurized air hose for the selective delivery of pressurized air to the pressure chamber 21.

Figure 2:
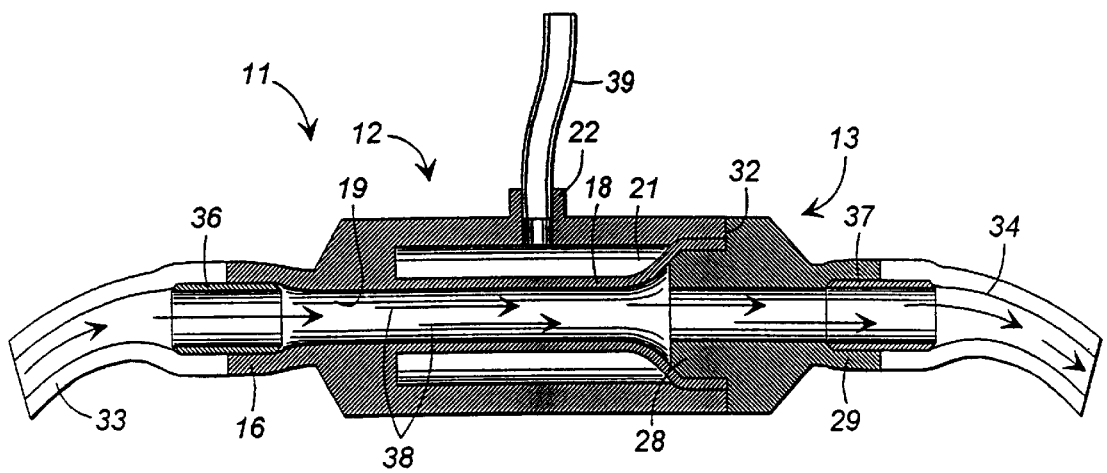
FIG. 2 is a cross-sectional view of the valve of assembly of FIG. 1 shown assembled, spliced in a fluid flow line, and in its open condition.

FIG. 2 illustrates the sphincter valve of this invention fully assembled and spliced into a fluid delivery line for controlling the flow of fluid therethrough. In FIG. 2, the valve is shown in its open condition allowing fluid to flow through the valve and through the fluid delivery line. The end cap 13 is seen inserted in the end of the main body 12 with the end of the interior tube 28 and the end of the pressure chamber stretched and sealed about the inwardly projecting plug 28. The shoulder is sealed against the end of the outer shell with an appropriate silicone adhesive to seal off the end of the pressure chamber 21.

One end 33 of the fluid delivery line is coupled to the coupling nipple 16 at the left end of the valve by means of a cylindrical adapter 36. Specifically, the adapter 34 fits tightly within both the end of the coupling nipple and the end of the delivery tube to couple the two together. Other coupling means can also be used. For example, the coupling nipple might simply be stretched, the end of the fluid delivery tube inserted, and the nipple released to constrict and seal about the end of the tube. These and other means of coupling the delivery tube to the valve are contemplated and are within the scope of the present invention.

Similarly, the other end 34 of the fluid delivery line is coupled via adapter 37 to the coupling nipple 29 at the other end of the valve. Again, while an adapter is used, other coupling means might be employed. Thus it is seen that the flow of fluid is free to continue from the left portion of the fluid delivery line, through the interior tube of the valve, and into the right portion of the fluid delivery line as if the valve were not in the system. A pressurized air supply line 39 is coupled to the coupling nipple 22 and communicates with the pressure chamber 21 within the valve. Through the supply line 39, pressurized air can be selectively injected into the pressure chamber for closing the valve as described in more detail below. In FIG. 2, no pressure has been applied to the pressure chamber and the valve is fully open allowing the free flow of fluid as indicated by arrows 38.

It will be appreciated from FIG. 2 that the flexible nature of the silicone material from which the valve is molded contributes to its functionality, allowing quick and easy coupling of the valve to the various tubes of the fluid delivery and pneumatic control systems. This represents and advantage over prior art sphincter valves with hard plastic shells, wherein the various tubes and supply lines must generally be coupled to the valve with ancillary clamps or other appropriate fasteners.

Figure 3:
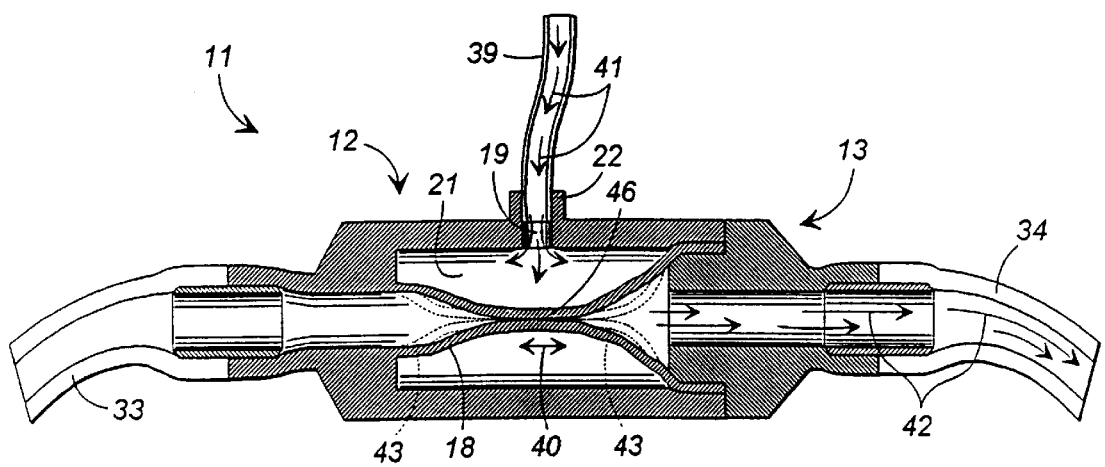
FIG. 3 is a cross-sectional view of the valve assembly shown assembled, spliced in a fluid flow line, and in its closed condition.

FIG. 3 illustrates operation of the sphincter valve of this invention to close off a flow of fluid and to provide a momentary pulse of fluid through the fluid delivery line. As in FIG. 2, the valve 11 is seen to be spliced into a fluid delivery line at the opposed ends of the valve. The pressurized air supply line 39 is coupled to the main body 12 at the coupling nipple 22 and is in communication with the pressure chamber 21 for delivery of pressurized air thereto. In FIG. 3, pressurized air, or other appropriate gas as desired, is shown at 41 being forced into the pressure chamber 21 through the pressurized air supply line 39. The pressurized air can originate from any appropriate source connected to the other end of the supply line 39 (not shown), such as, for example, a pump or pressurized air tank and associated control system, a hand operated pump, or other source. The actual means of delivering pressurized air to the pressure chamber can vary widely depending upon the particular application to which the valve is put.

As pressurized air is delivered to the pressure chamber 21, the pressure within the chamber gradually increases as a function of the rate of pressurized air flow. This, in turn, exerts increasing inward force on the interior tube 18 and corresponding outward force on the interior walls of the outer shell 17. Since the walls of the interior tube are substantially thinner than the walls of the main body, the increasing force causes the interior tube to begin to collapse upon itself. Eventually, the force becomes sufficient to cause the walls of the interior tube 18 to meet and contact each other intermediate the ends of the tube as illustrated at 46 in FIG. 3. At this point, the flow of fluid through the fluid delivery line is shut off and the valve is in its closed condition.

If desired, pressurized air can continue to be forced into the pressure chamber 21 after the initial closing of the valve. This further increases the pressure within the pressure chamber 21 causing the interior tube 18 to collapse further upon itself from its mid-portion toward its opposed ends, as illustrated in phantom lines at 43 in FIG. 3. This action, in turn, squeezes out fluid within the interior tube causing a surge or pulse of fluid through the fluid delivery line as indicated at 42 in FIG. 3. It has been found that the flexible unitary nature of the entire valve assembly, including the walls of the main body, improves the efficiency of this process as the main body walls bulge slightly outwardly in response to the increasing pressure.

The pulse action of the sphincter valve of this invention provides significant advantages in many applications, and particularly in colonic lavage procedures. In such procedures, the valve can be opened and closed rapidly up to several times per second if desired. This causes a distinctly but gently pulsed flow of fluid into a patient's colon as a result of the surge or pulsed action provided by the opening and closing valve. Such a pulsed flow has been found to be very beneficial in colonic lavage procedures for dislodging and hydrating impacted fecal material in a patient's colon so that the material can be removed from the colon through an associated drain line. Thus, the unique sphincter valve of the present invention provides benefits and advantages and does so at a cost and with a complexity far less than prior art sphincter valves. Thus, the valve can simply be discarded after use, making it ideal for disposable fluid delivery kits for use in medical procedures. Disposability is important in many medical procedures and particularly procedures such as colonic lavage performed at home because the valves become contaminated after use and cannot easily be cleaned. Further, the valve of this invention is relatively soft and is not uncomfortable to the skin of a patient. It can thus be rested on a patient's skin during a procedure if necessary without being uncomfortable.

Figure 4:
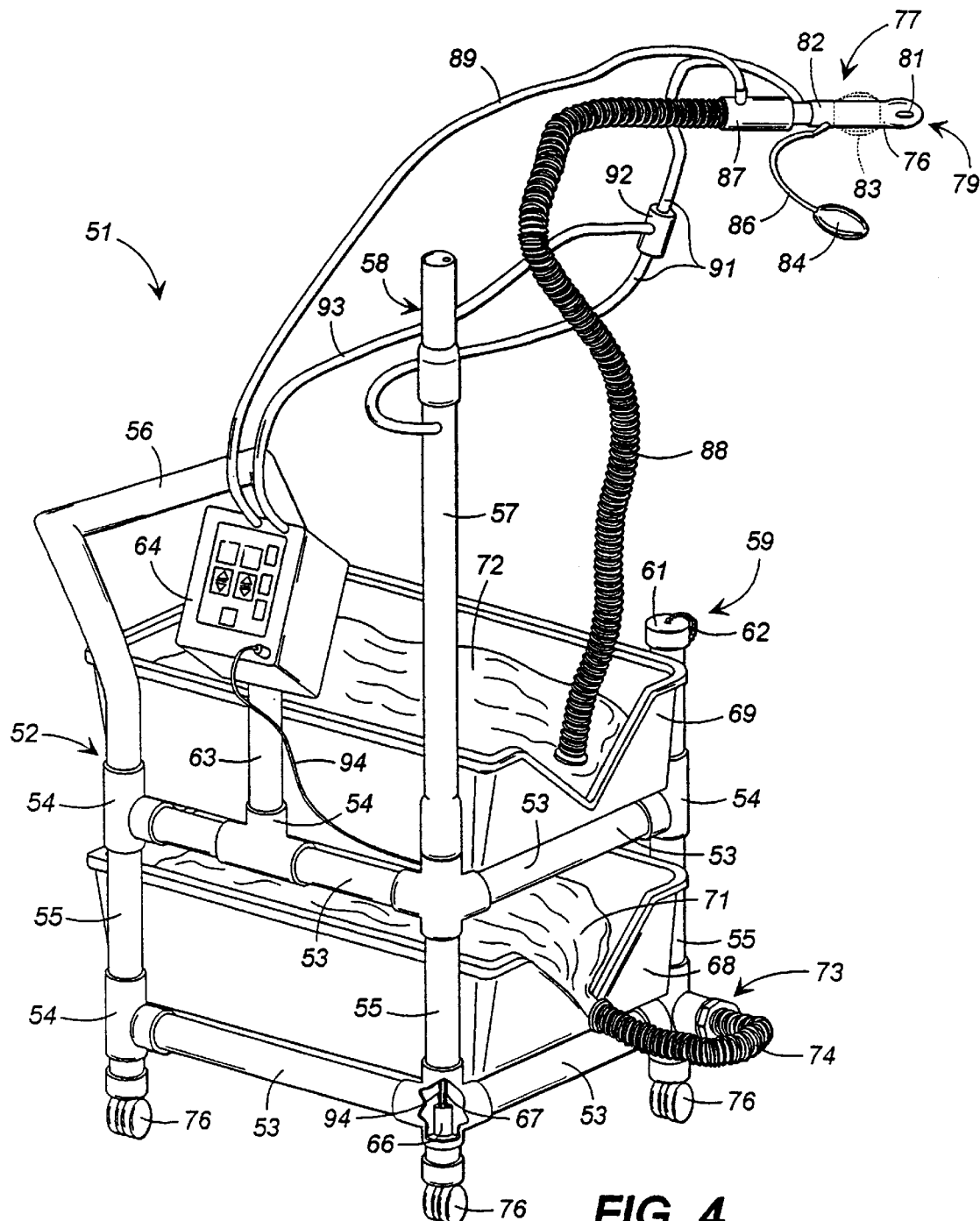
FIG. 4 is a perspective view of a colonic lavage apparatus that embodies principles of the present invention in a preferred form.

FIG. 4 illustrates a colonic lavage apparatus that incorporates the sphincter valve of FIGS. 1 through 3 and that further embodies principles of the present invention in a preferred form. The apparatus 51 comprises a portable frame 52 that is generally constructed of tubular PVC pipe sections connected together with appropriate PVC fittings 54 to form a frame having a substantially sealed interior cavity for containing lavage liquid. More specifically, the frame has horizontal rails 53 that extend between upwardly projecting legs 55 of the frame. A contoured U-shaped handle 56, also preferably made of tubular PVC, is connected to the tops of the two back legs of the frame to provide a means for pushing the frame along a floor. To facilitate such portability, casters 76 are attached to the bottom end of each leg 55.

A regulator tower 57 extends upwardly from the top end of one of the front legs 55 of the frame and is capped with a regulator valve assembly 58, which is described in more detail below. The top of the other front leg 55 terminates in an upwardly open filler port 59 for filing the interior cavity of the frame with a lavage liquid. A filler cap 61, preferably tethered to the frame by a chain 62, covers the upwardly open filler port during normal operation of the apparatus.

A controller support arm 63 is coupled to and extends upwardly from one of the horizontal rails 53 of the frame and is configured to support a computer based controller 64 for controlling the various functions of the apparatus as detailed below.

The lower horizontal rails 53 of the frame 52 form a cradle that is sized to receive and carry a lower plastic tray 68, which preferably is formed of molded plastic. Similarly, the upper horizontal rails 53 form a cradle that is sized to receive and hold an upper tray 69. The lower tray 68 is sized to contain a lavage liquid reservoir 71, which, in the preferred embodiment, comprises a sealed plastic bag that rests in the tray 68. Similarly, the upper tray 69 is sized to contain a waste liquid receptacle 72, which also preferably comprises a sealed plastic bag. The plastic bags forming the reservoir 71 and receptacle 72 are intended to be single use disposable items and forming these elements from inexpensive plastic bags facilitates this purpose.

During normal use of the apparatus 51, the lavage liquid reservoir 71 is coupled to the sealed interior cavity of the frame 52 through a flexible hose 74 communicating at one end with the reservoir 71 and at its other end with a fitting 73 on one leg of the frame. In this way, as the sealed hollow frame is filled with a lavage liquid through its filling port 59, the lavage liquid flows through the flexible hose 74 and fills the lavage liquid reservoir 71. Thus, the reservoir 71 provides a lavage liquid capacity that is substantially greater than the capacity of the sealed interior cavity of the frame alone.

A lavage liquid delivery and waste removal assembly 77 forms a part of the colonic lavage apparatus 51. The assembly 77 comprises a speculum 78 that is configured and sized to be inserted into a patient's rectum for delivering a colonic lavage. The speculum 78, which preferably is molding from a unitary piece of rubberized material such as silicone, has a generally tubular body with a closed bulbous distal end 79. A pair of oblong openings 81 are formed in the distal end of the speculum 78 for delivering lavage liquid to a colon and receiving waste liquid for extraction from the colon. A selectively inflatable cuff 83 is provided on the tubular body portion 82 of the speculum 78 and can selectively be inflated and deflated by use of a squeeze bulb 84. The specific configuration and operation of the speculum 78 is described in more detail below.

The speculum 78 is secured at its open back end to a first sphincter valve 87. Preferably, the sphincter valve 87 is molded from a unitary piece of rubberized material such as silicone and has the configuration described hereinabove with reference to FIGS. 1 through 3. A waste tube or conduit 88 communicates between the sphincter valve 87 and the waste liquid receptacle 72 carried by the upper tray 69. Thus, the sphincter valve 87 is mounted in line with the waste liquid tube 88. It will be understood that, with this configuration, when the sphincter valve 87 is in its open configuration, waste liquid is free to flow through the openings 81 in the speculum 78, through the open sphincter valve, and to the waste liquid receptacle 72 through the tube 88. Conversely, when the sphincter valve 87 is closed, this path is blocked and waste liquid does not flow out of a patient's colon. The sphincter valve 87 is pneumatically operated by means of air pressure selectively supplied through a control tube 89 that, in turn, is connected to the controller 64. The controller 64 is programmed and adapted to supply pressurized air for opening and closing the sphincter valve 87 according to a predetermined cycled schedule for optimizing the colonic lavage procedure.

A pump 66, which preferably is a commercially available submersible marine pump, is located within the sealed interior cavity of the frame in the left front leg thereof. Thus, when lavage liquid fills the frame, the pump 66 is submerged in the lavage liquid. Activation of the pump 66 by means of an appropriate command issued over the pump control line 94 from the controller 64 causes the pump 66 to deliver lavage liquid upwardly through a tube 67 to the top portion of the regulator tower 57. From there, the pressure of the lavage liquid is regulated, as detailed below, and is delivered to the speculum 78 through a lavage liquid supply tube 91. Connected in line with the supply tube 91 is a second sphincter valve 92, which preferably also has a unitary rubberized structure according to the present invention. The second sphincter valve 92 is coupled to the controller 64 through a control tube 93. The controller 64 is programmed and adapted to supply pressurized air selectively to the second sphincter valve 92 for opening and closing the valve according to a predetermined schedule. Significantly, the controller also has the capability of cycling the sphincter valve 92 in relatively rapid succession during an inflow cycle in order to provide a gently pulsed supply of lavage liquid to the colon of a patient under treatment.

While the first and second sphincter valves 87 and 92 have been illustrated as separate devices in FIG. 4, it should be understood that, according to the present invention, these valves could be molded together in a single unit from a rubberized material such as silicone. In such a case, the valves would be co-located, preferably close to the speculum 78, and the associated supply, drainage, and control tubes would be connected to the tandem valve assembly appropriately.

When using the colonic lavage apparatus of FIG. 4, a disposable single use package containing the speculum, sphincter valves, plastic bag liquid reservoirs, and associated tubing is supplied. These items are then positioned and connected as shown in FIG. 4. The sealed interior cavity of the frame 52 is then filled with lavage liquid through the filling port 59 to a predetermined volume. As the sealed interior cavity is filled, lavage liquid also flows through the flexible hose 74 and fills the lavage liquid reservoir 71 within the lower tray 68. The filling process is complete when the apparatus has been filled with a sufficient volume of lavage liquid to perform a colonic lavage procedure on a patient.

With the system charged with lavage liquid, the speculum 78 is inserted through a patient's rectum until it is properly positioned within the patient's colon. The inflatable cuff 83 is then inflated by squeezing the squeeze bulb 84. This causes the cuff 83 to bear against the inside walls of the patient's colon to form a seal so that lavage and waste liquid do not leak past the body of the speculum 78. For this purpose, the squeeze bulb 84 is provided with a screw valve so that when the cuff 83 has been properly inflated, the screw valve can be closed to maintain the inflated condition of the cuff.

At this point, a nurse or other attendant selects by pressing appropriate buttons on the controller 64 the desired lavage cycle and timing sequence for the patient. By timing sequence it is meant the sequence in which the controller activates the pump 66 and the two tube sphincter valves 87 and 92 to provide controlled inflow of lavage liquid into the patient's colon and controlled outflow of waste liquid from the colon. In one preferred sequence, for example, the controller automatically begins the lavage procedure by activating the pump 66, opening the inflow valve 92, and closing the outflow valve 87. This causes lavage liquid to flow through the speculum 78 into the patient's colon. Preferably, and most significantly, it has been found that, during this inflow cycle, it is highly desirable to open and close the sphincter valve 92 at a rate of about four cycles per second. The opening and closing of the valve 92 during the inflow cycle has been found to induce a gently pulsed wave characteristic in the inflowing liquid stream. This pulsing action has been found to enhance significantly the ability of the inflowing lavage liquid to break up and dissolve impacted waste material in the colon. It has also been found through clinical trials that the pulsing of the inflowing lavage liquid triggers autonomic peristaltic action in the patient's colon, which further loosens and breaks up impacted waste material. The result has been a substantially enhanced performance over prior art colonic lavage methods.

Once a predetermined amount of lavage liquid has been delivered in this pulsed fashion to the colon, the controller then closes both the inflow and outflow sphincter valves 87 and 92 respectively to hold the lavage liquid in the colon for a predetermined length of time. This further dissolves and loosens impacted waste material in the colon and enhances the effectiveness of the procedure.

When the hold cycle has terminated, the controller opens the outflow sphincter valve 87 while maintaining the inflow sphincter valve 92 in its closed configuration. Thus, waste liquid bearing dissolved waste material from the colon is expunged from the colon through the openings in the speculum 78, through the sphincter valve 87, and to the waste receptacle 72 through the waste tube 88. The entire cycle can then be repeated either with the same timing characteristics or with different timing characteristics until the patient's colon is completely cleaned.

It should be understood that the just described sequence represents only one preferred sequence of providing a colonic lavage with the apparatus of this invention. Virtually endless sequences are possible with the computer based controller 64. Further, the timing of the inflow and outflow cycles, the timing of the hold cycle, and the rate at which the inflowing liquid is pulsed during the inflow cycle are all variable and selectable by the user, either from preprogrammed sequences or through user programmed or manual mode operation of the controller. For instance, it has been found desirable that for each repetition of inflow and outflow in the sequence described above, the inflow times, outflow times, and hold times be progressively increased until a predetermined number of cycles have been completed or a predetermined amount of lavage liquid has been used and this is easily accomplished by appropriately programming the controller. Virtually any combination of inflow, outflow, and hold cycles as well as various pulsing characteristics are possible with the colonic lavage apparatus of this invention and all are considered to be within the scope thereof.

FIGS. 5 and 6 illustrate the regulator valve assembly 58 that is located atop regulator tower 57. The regulator valve assembly 58 functions to ensure that lavage liquid is never delivered to the colon of a patient at a pressure above a predetermined threshold. A virtually 100% reliable regulator is necessary in this regard because of the possibility of colon damage should liquid be delivered at a pressure that is too great. The regulator valve assembly 58 comprises a regulator housing 96 that is mounted atop the regulator tower 57. A first plug 97 is mounted in the regulator housing 96 near the bottom thereof and a second plug 98 is mounted above and spaced from the lower plug 97. The plugs 97 and 98 can be made of a rubberized material or, alternatively, can be formed of PVC and cemented in place within the housing. A regulator tube 104 extends through the lower plug 97 and upwardly through a center passageway in the upper plug 98. The regulator tube 104 terminates in a valve seat 106 having a lip portion that projects slightly above the top of the plug 98. The lower portion of the regulator tube 104 is connected to a "T" 103 that is coupled both to the pump tube 102, which extends upwardly through the regulator tower from the pump 66, and to the lavage liquid supply tube 91, which communicates with the speculum 78 through sphincter valve 92.

A cap 99 having a weep hole 101 is secured to the top of the regulator housing 96 forming a compartment in the top portion thereof. A weighted stainless steel ball 107 is captured in the compartment and, under normal conditions, rests atop the valve seat 106. The mouth of the valve seat is sized and configured such that a seal is formed between the mouth of the seat and the ball 107 as a result of the force of gravity pressing the ball against the mouth of seat.

A set of overflow return holes 108 are formed through the plug 98 and, as described in more detail below, allow overflow lavage liquid to flow downwardly through the plug 98. A drain tube 111 also extends through the lower plug 97 and terminates in a drain 109. In this way, overflow lavage liquid that flows through the overflow return holes 108 in the upper plug 98 is directed through the drain 109 and the drain tube 111 back to the lower extremities of the sealed cavity formed by the frame and thus back to the lavage liquid reservoir therein. Thus, it will be seen that the regulator valve assembly 58 functions in conjunction with the frame 52 to form a closed system whereby overflow lavage liquid is automatically directed back to the reservoir of liquid for further use.

In operation, when the pump 66 is activated, lavage liquid is pumped upwardly through the pump tube 102 and is delivered through the T 103 to the delivery tube 91 and then on to the speculum. As long as the pressure of the liquid being delivered by the pump is below a predetermined threshold, the liquid flows directly from the pump to the speculum in the expected way. However, if the pressure of the liquid should exceed a predetermined value, it is then sufficient to lift the weighted ball 107 off of the valve seat 106 allowing excess lavage liquid 105 to escape and flow back down to the liquid reservoir. The pressure threshold is determined by the weight of the weighted ball 107. For example, a heavier ball would result in a higher threshold pressure while a lighter ball would result in a lower threshold pressure. In practice, it has been found that the weight of the ball should be selected to provide a threshold pressure of between about 2 and 2.5 psi in order to assure a safe and effective procedure for a wide variety of patients. A stainless steel ball having a diameter of about 1 and $\frac{1}{16}$ inch and a corresponding weight of about 0.247 lbs. has been found to provide such a threshold.

In addition to regulating the pressure of lavage liquid inflow, the gravity actuated valve assembly 58 has been found to provide an additional advantage for use in the present invention. Specifically, when the pressure of lavage liquid reaches the predetermined threshold, the ball 107 has been found not simply to rise in response to the pressure, but to bob up and down at a relatively rapid rate atop the valve seat 106. This causes the pressure of the lavage liquid to oscillate as it is delivered to the speculum. Such supplemental oscillation of the pressure, in conjunction with the normal pulsing of the inflow sphincter valve, enhances even further the ability of the lavage liquid to dislodge impacted waste material within the patient's colon and renders the process even more efficient and effective.

FIG. 6 is a top plan view of the upper plug 98 of FIG. 5. The valve seat 106 can be seen centered within the plug for proper positioning of the weighted ball 107. A set of overflow return holes 108 are arrayed around the valve seat 106 to permit overflow lavage liquid to flow freely back to the reservoir in the bottom of the sealed cavity of the frame 52.

Figure 7:
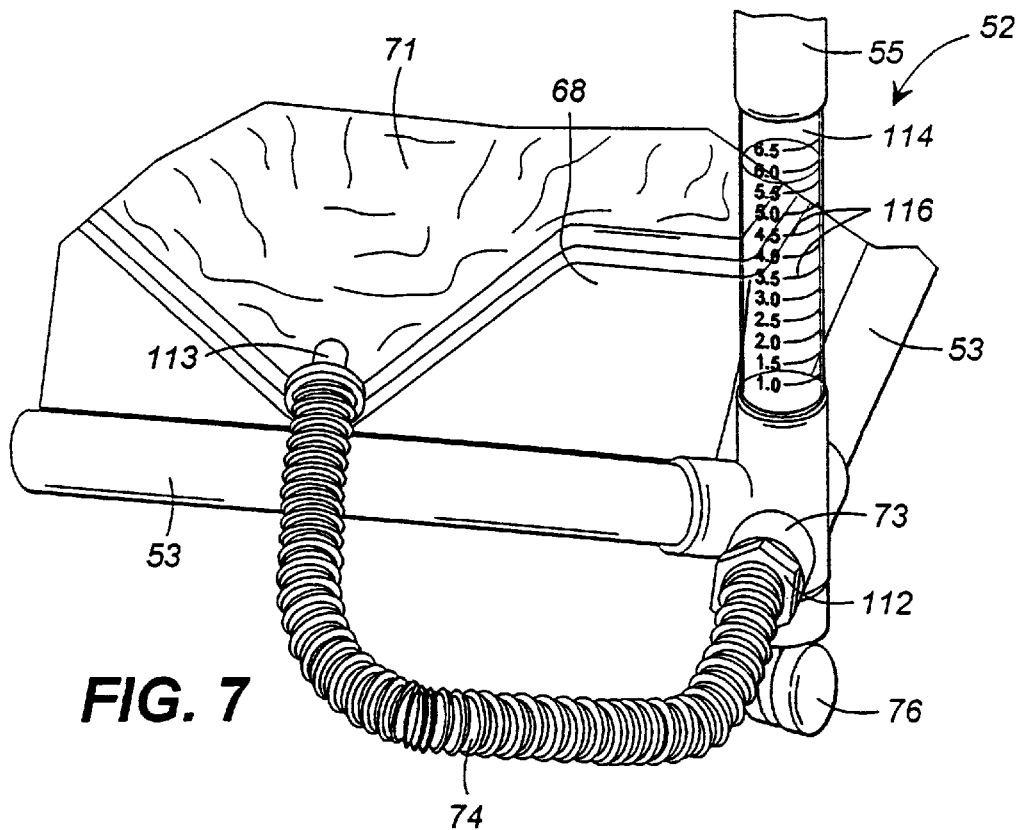
FIG. 7 is a partial perspective view of the frame of the apparatus of FIG. 4 illustrating the containing of lavage liquid therein and the coupling to a lavage liquid receptacle carried by the frame.

FIG. 7 is a perspective view of the lower right corner of the frame 52 as seen in FIG. 4. The lower portion of the vertical leg 55 is seen to incorporate a clear section 114 that forms a liquid level gauge for filling the frame and reservoir 71 with lavage liquid. A set of markings or indicia 116 are provided on the gauge and preferably are calibrated in units of liquid volume such as gallons so that the system can be charged with the proper amount of lavage liquid for a given process.

The sealed interior cavity of the frame 52 is in fluid communication with the lavage liquid reservoir 71 through a flexible hose 74. The hose communicates at one end through a coupling nipple 113 to the plastic bag reservoir 71 and communicates at its other end with the sealed interior cavity of the frame through a threaded adapter 112 and a fitting 73. The level at which the tray 68 is supported on the frame is such that the plastic bag reservoir 71 fills simultaneously with the sealed interior cavity of the frame 52 and the indicia 116 are calibrated to indicate the total amount of lavage liquid contained in the frame and in the plastic bag reservoir 71. The reservoir 71 is necessary to provide a sufficient capacity to complete a colonic lavage treatment on an average patient, which, for example, might be between about five gallons and six gallons of liquid. As the colonic lavage is administered to a patient, the lavage liquid is progressively drawn out of the frame and the reservoir 71 by the pump 66 until both are substantially drained of lavage liquid.

Figure 8:
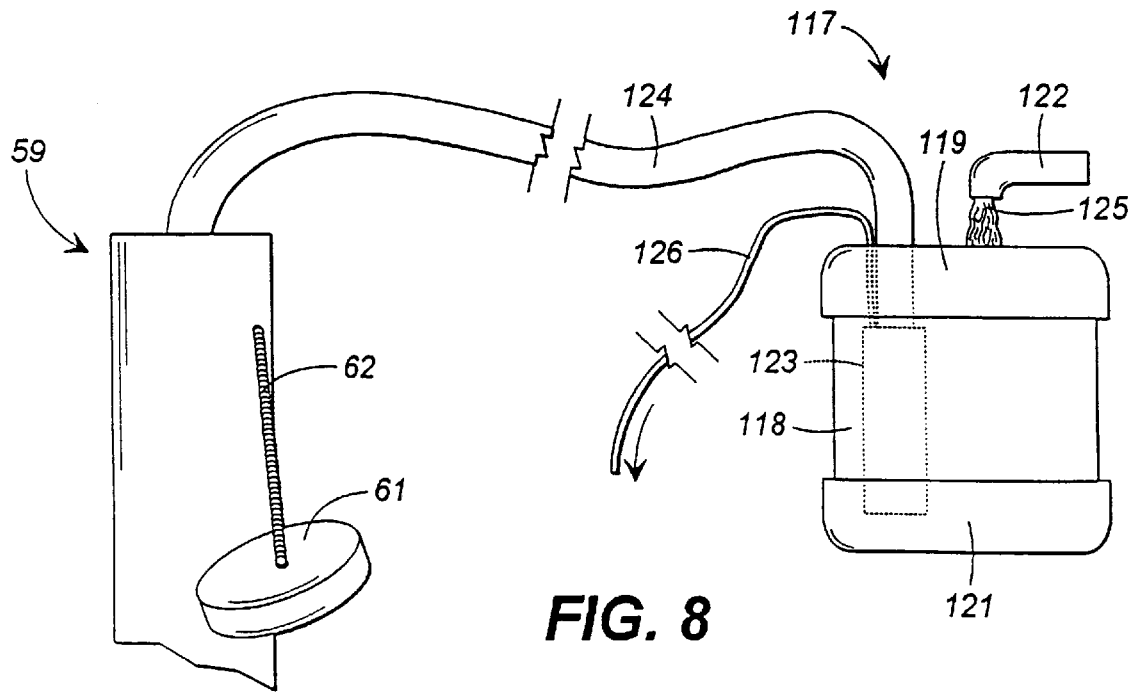
FIG. 8 illustrates a preferred method and apparatus for filling the hollow tubular frame of this invention with a lavage liquid.

FIG. 8 illustrates a preferred method and apparatus for filling the device of this invention with lavage liquid prior to administering a colonic lavage. The system is charged with lavage liquid through the filler port 59 at the top of the front right leg of the frame as seen in FIG. 1. To accomplish the filling, the cap 61 is removed to permit access to the interior cavity of the frame. A filler module is provided for charging the system with lavage liquid, which, in most cases, is ordinary warmed tap water. The filler module 117 comprises a housing 118 closed at its bottom with a bottom cap 121 and at its top with a top cap 119. The housing 118 contains a submersible pump 123, which can be the same type as pump 66 in the frame 52. The pump is coupled to one end of a filler hose 124 and the other end of the hose is adapted to be inserted through the filler port 59 of the frame. A control wire 126 electrically connects the pump 123 to a source of electrical power, which can be the controller module 64. The top cap 119 of the filler module 117 has an opening (not visible in FIG. 8) through which the housing 118 can be filled with water 125 from a faucet 122 or can be filled with another appropriate lavage liquid if desired. As the filler module is filled with water, the pump 123 delivers the water from the module, through the filler hose 124 to the filling port 59 of the frame 52. Therefore, water 125 is gradually pumped from a flowing faucet at a sink or other convenient location to the colonic lavage apparatus until the apparatus is fully charged with lavage liquid. At this point, the faucet is turned off and the filler module 117 is stowed for future use. Accordingly, with the filler module of FIG. 8, the charging of the present invention with lavage liquid is simple, easy, clean, and does not require lifting of water by the operator. This represents a distinct advantage over prior art colonic lavage devices.

FIG. 9 illustrates the present invention embodied in a portable carryable unit that can be transported easily with a patient on vacations and other trips. The embodiment of FIG. 9 includes many of the elements previously described with respect to FIGS. 4–8 and elements already described in detail will not be described in detail again here.

The embodiment of FIG. 9 includes a carrier 132 that, preferably, is a cloth or nylon bag having a shoulder strap 137 to allow the bag to be carried easily by one person. The carrier 132 is formed to define a liquid reservoir compartment 133 on one side of the carrier and a waste receptacle compartment 134 on the other side of the carrier. Each of the compartments 133 and 134 can be accessed through respective zippers 136 provided along the top of the carrier. The carrier 132 is sized to contain all of the elements illustrated in FIG. 9 so that the entire apparatus can easily be carried from place to place in the carrier 132. The colonic lavage apparatus is illustrated in FIG. 9 with all the components assembled and prepared for delivering a colonic lavage. It should be understood, however, that during transportation, the elements are disassembled and inserted into one of the compartments of the carrier.

The colonic lavage apparatus in FIG. 9 further comprises a generally "F" shaped hollow pump housing 138 that is formed form tubular PVC plastic material. The pump housing 138 includes a horizontal chamber 139, an overflow tower and level gauge 141, and a pump tower 142. The overflow tower and level gauge 141 preferably is formed of clear plastic material with indicia printed thereon to indicate a volume of lavage liquid. The hollow pump housing 138 is removably attached to the outside of the carrier 132 during use of the apparatus with a set of Velcro strips 143 that wrap around the pump housing to hold it in place. The pump housing 138 is coupled through a flexible hose 146 and a threaded adapter 144 to a lavage liquid receptacle positioned within the liquid reservoir compartment 133. Preferably, the receptacle is a plastic bag as illustrated in the prior embodiment and the carrier 132 is provided with an opening 145 through which the flexible hose 146 extends to the plastic bag.

A lavage liquid delivery and waste removal assembly 147 is provided and, in the preferred embodiment, is the same as assembly 77 illustrated in FIG. 4. In general, the assembly 147 comprises a speculum 148 for insertion through a patient's rectum. The speculum 148 is in fluid communication through a sphincter valve 149 and a flexible hose 151 to a waste liquid receptacle located in the waste receptacle compartment 134. Preferably, the waste liquid receptacle comprises a disposable plastic bag that is gradually filled during the lavage process and can be discarded thereafter. The sphincter valve 149 is coupled through a control tube 166 to the controller 164, which provides compressed air to the sphincter valve 149 to open and close it according to a pre-determined schedule.

A submersible electric pump (not visible in FIG. 9) is located inside the pump tower 142 and is activated by the controller 164 by means of a pump control wire 168. A collapsible regulator tower 152 is provided with feet 153 and a vertically extending stantion 156 formed by disconnectable sections 157. The tower 152 is topped by a regulator valve assembly 158, which preferably is the same as the regulator assembly 58 described in conjunction with FIG. 4. Upon activation of the pump within the pump tower 142, lavage liquid contained within the housing 138 is pumped through tube 162 upwardly to the top portion of the regulator tower 152. As with FIG. 4, the tube 162 is coupled within the tower 152 to a T and then on through supply tube 159 and sphincter valve 161 to the speculum 148. The other leg of the T within the tower 152 is coupled to the weighted ball regulator valve within the regulator assembly 158 as shown in FIG. 4. Overflow liquid resulting from operation of the regulator valve is delivered through an overflow tube 163 back to the housing 138 through the top of the overflow tower 141. The sphincter valve 161 is coupled to and controlled by the controller 164 through a control tube 167.

In use, the components illustrated in FIG. 9 can be disassembled and stowed within the carrier 142 for transport from one place to another. Specifically, the two plastic bags that form the lavage liquid reservoir and waste liquid receptacles are placed in the carrier 132 as is the pump housing 138, the assembly 147, and all the associated hoses and tubes. The regulator valve tower 152 is then disassembled by removing its feet 153 and disconnecting the vertical sections 157 from each other. All of these components are then placed within the carrier 132 as is the controller 164. The zippers 136 are then zipped and the entire apparatus can easily be carried across one's shoulder.

For use in delivering a colonic lavage, the elements are removed from the carrier and positioned and assembled as shown in FIG. 9. The lavage liquid reservoir bag is positioned in compartment 133 and connected through hose 146 to the housing 138. The housing 138 is then filled with lavage liquid, which can be warm water, through the top of one of the towers 141 and 143. As the housing 138 is filled, the lavage liquid flows into the lavage liquid reservoir contained within the compartment 133 and the filling procedure is stopped when the liquid is indicated to be at the proper level. A colonic lavage can then be performed as described above to remove impacted fecal material from a patient's colon. After the procedure, the plastic bags, tubes, sphincter valves, and any other components of the system that come in contact with lavage liquid or waste liquid are simply discarded and a new sterilized disposable packet containing the same items is used for the next procedure.

Accordingly, it will be seen that the embodiment illustrated in FIG. 9 has unique advantages in situations where a patient desires to travel from one place to another such as, for example, to travel on a vacation or other trip. No longer does the patient have to go to a facility to receive a colonic lavage can have the procedure performed privately and easily wherever he or she goes.

FIG. 10 illustrates a preferred embodiment of a disposable speculum for use with the present invention. The speculum 171 preferably is molded from a unitary piece of rubberized material such as, for example, silicone. The speculum can also be molded from latex-based materials if desired; however, some patients may have latex allergies and latex materials are therefore not preferred.

The speculum 171 has a generally tubular hollow body 172, an open proximal end 173, and a contoured closed distal end 174 that is slightly bulbous in nature. The distal end 174 of the speculum is provided with opposing oval shaped openings 176 (only one of which is visible in FIG. 10) through which lavage liquid passes into a patient's colon and through which waste liquid passes from the colon and through the speculum for disposal.

An inflatable rubber cuff 177 is disposed about the tubular body 172 of the speculum and is made of a thin rubber material that can be blown up or inflated as illustrated in FIG. 10. To facilitate such inflation, the speculum 171 is molded with an air pressure passageway 178 that terminates in a nipple 179. The nipple 179, in turn, is coupled to the tube of a squeeze bulb as illustrated in FIG. 4. In use, the inflatable cuff 177 can be inflated by squeezing the squeeze bulb which causes compressed air to travel through the air pressure passageway 178 and into the inflatable cuff 177. As described above, the cuff 177 expands to engage the walls of a patient's colon to prevent accidental leakage of lavage liquid or waste liquid during the lavage procedure. When the lavage procedure is over, the screw valve on the squeeze bulb is simply released to deflate the cuff 177 for removal of the speculum 171.

The invention has been described herein in terms of preferred embodiments and methodologies. It will be apparent to those of skill in the art, however, that various modifications might well be made to the illustrated embodiments within the scope of the invention. For example, while silicone or a silicone compound has been illustrated as the preferred material from which the valve is molded, other appropriate materials might well be substituted. Further, the size and relative dimensions of the various components of the valve might be different from those illustrated in the drawings depending upon the particular purpose for which it is intended. For example, the valve could be made long and thin in order to increase the relative length of the interior tube and provide a more pronounced pulsed action as the valve is closed. Also, the sphincter valve of this invention has been illustrated and described as a pneumatically controlled device wherein air or gas is used to open and closed the valve. In certain applications, however, it might be desirable to employ a fluid to open and close the valve rather than air. In such cases, the valve would be hydraulically controlled rather than pneumatically controlled, but the principles of operation would remain substantially the same. The valve has also been described in terms of a single unitarily molded structure. The same principles could be applied to a unitarily molded gang valve wherein two or more individually controllable valves are molded within a single unitary body. Finally, the apparatus for delivering a colonic lavage and its various components as described herein may well be constructed with a wide variety of shapes and configurations that could differ from the illustrated embodiments. These and other additions, deletions, and modifications might well be made to the disclosed embodiments by those of skill in the art without departing from the spirit and scope of the invention as set forth in the claims.

What is claimed is:

1. An apparatus for delivering a colonic lavage, said apparatus comprising:

a frame constructed of substantially hollow tubular elements connected together to form a sealed interior cavity for containing a lavage liquid;

means for selectively filling said interior cavity with a lavage liquid;

a waste receptacle carried on said frame for receiving and containing waste material resulting from a colonic lavage;

a speculum for delivering the lavage liquid to the interior of a colon and for receiving waste from the colon;

a waste conduit communicating at one end with said speculum and at its other end with said waste receptacle for delivering waste from the colon to said waste receptacle;

a first valve for selectively opening up and closing off said waste conduit;

delivery means in said frame for delivering lavage liquid from said interior cavity of said frame to said speculum for injection into a colon;

a delivery conduit coupling said delivery means with said speculum for delivery of lavage liquid thereto;

a second valve means for selectively opening up and closing off said delivery conduit; and control means for alternately opening up and closing off said second valve means according to a predetermined schedule to deliver a pulsed supply of lavage liquid to a colon for dislodging impacted fecal material therefrom for delivery through said waste conduit to said waste receptacle.

2. An apparatus for delivering a colonic lavage as claimed in claim 1 and wherein said control means is further adapted to open up and close off said first valve means according to a predetermined schedule for creating a pulsed drainage of waste from the colon to said waste receptacle.

3. An apparatus for delivering a colonic lavage as claimed in claim 2 and further comprising a regulator for maintaining the pressure under which lavage liquid is delivered to the colon below a predetermined threshold.

4. An apparatus for delivering a colonic lavage as claimed in claim 3 and wherein said regulator includes a weighted ball disposed atop an orifice coupled to said delivery conduit, the weight of said ball being predetermined so that pressure of lavage liquid in said delivery conduit above said predetermined threshold causes said weighted ball to be displaced from said orifice to relieve the excess pressure and maintain the delivery pressure at the predetermined threshold.

5. A device for delivering a colonic lavage comprising a substantially hollow sealed frame configured to carry selected elements of said device, means for filling said frame with a lavage liquid, a pump in said frame for delivering lavage liquid to a colon, a regulator in said frame for regulating the pressure at which lavage liquid is delivered to a colon, and means for pulsing the delivery of lavage liquid to a colon according to a predetermined time schedule to dislodge waste material from the colon for removal.

6. A device for delivering a colonic lavage as claimed in claim 5 and further comprising a speculum insertable into a colon, and a tubular conduit coupling said pump to said speculum for delivering lavage liquid to a colon through said speculum.

7. A device for delivering a colonic lavage as claimed in claim 6 and wherein said means for pulsing the delivery of lavage liquid comprises a first sphincter valve coupled in line with said tubular conduit and control means coupled to said first sphincter valve for selectively opening and closing said sphincter valve according to a predetermined schedule for pulsing the delivery of lavage liquid according to the schedule.

8. A device for delivering a colonic lavage as claimed in claim 7 and further comprising a waste receptacle carried by said frame and a waste conduit communicating at one end with said speculum and at its other end with said waste receptacle for directing waste material from a colon to said waste receptacle for disposal.

9. A device for delivering a colonic lavage as claimed in claim 8 and further comprising means for selectively opening up and closing off said waste conduit.

10. A device for delivering a colonic lavage as claimed in claim 9 and wherein said means for selectively opening up and closing off said waste conduit comprises a second sphincter valve coupled in line with said waste conduit, said control means opening and closing said second sphincter valve according to a predetermined time schedule.

11. A device for delivering a colonic lavage as claimed in claim 10 and wherein said control means is configured for alternately opening said first sphincter valve while closing said second sphincter valve and closing said first sphincter valve while opening said second sphincter valve for alternately delivering lavage liquid to a colon and then draining dislodged waste from the colon in a pulsed manner to evacuate the colon.

12. A device for delivering a colonic lavage as claimed in claim 11 and wherein said control means comprises a computer controller controlling pneumatic valves coupled to said first and second sphincter valves, said computer controller being programmed to actuate said pneumatic valves to deliver compressed air to said first and second sphincter valves to open and close said sphincter valves according to the predetermined schedule.

13. A device for delivering a colonic lavage as claimed in claim 12 and wherein said first and second sphincter valves are each molded from a unitary piece of pliable material.

14. A device for delivering a colonic lavage as claimed in claim 13 and wherein said speculum is molded from a unitary piece of pliable material.

15. A device for delivering a colonic lavage as claimed in claim 14 and wherein said speculum is provided with an inflatable exterior cuff and further comprising means for selectively inflating said cuff for sealing said speculum against the walls of a colon in which it is located.

16. A device for delivering a colonic lavage as claimed in claim 6 and wherein said regulator comprises an upwardly open orifice coupled to said tubular conduit and a weighted ball resting atop said orifice, the weight of said weighted ball being predetermined so that said weighted ball is lifted from said orifice when pressure within said tubular conduit rises above a predetermined threshold to relieve the excess pressure within said tubular conduit.

17. A device for delivering a colonic lavage as claimed in claim 16 and wherein said regulator is incorporated into said sealed frame and wherein lavage liquid released when said weighted ball is lifted from said orifice remains in said hollow sealed frame for reuse.

18. A device for delivering a colonic lavage as claimed in claim 5 and further comprising a lavage liquid reservoir carried by said frame and a conduit communicating between said hollow sealed frame and said lavage liquid reservoir for supplying said hollow sealed frame with lavage liquid from said lavage liquid reservoir.

19. In a colonic lavage apparatus for delivering lavage liquid to the colon of a patient and draining dislodged waste from the colon to a waste receptacle, the improvement comprising a frame constructed of tubular elements forming a sealed interior cavity, the lavage liquid being stored in said sealed interior cavity prior to delivery to a colon.

20. The improvement of claim 19 and further comprising a pump in said interior cavity positioned to be immersed in lavage liquid contained therein for pumping the lavage liquid to a colon.

21. The improvement of claim 20 and further comprising a regulator valve in said interior cavity coupled to said pump for regulating the pressure at which lavage liquid is delivered to a colon.

22. The improvement of claim 21 and wherein said frame is configured to carry said waste receptacle.

23. The improvement of claim 22 and further comprising control means for delivering lavage liquid to a colon in a pulsed stream and for draining waste from the colon in an alternately phased pulsed stream.

24. A portable apparatus for delivering a colonic lavage to a patient, said apparatus comprising:

a portable carrier for containing functional elements of the apparatus when being transported;

a lavage liquid reservoir stowable in said carrier for containing lavage liquid to be delivered to a colon;

a waste reservoir stowable in said carrier for receiving and containing waste material from a colon for disposal;

a substantially hollow pump housing stowable in said carrier during transportation and attachable to the exterior of said carrier during use of said apparatus, said pump housing containing a lavage liquid pump;

conduit means for selectively coupling said pump housing to said lavage liquid reservoir for receiving lavage liquid from said reservoir;

a speculum stowable in said carrier during transportation and insertable into the patient's colon, said speculum being configured to deliver lavage liquid to the colon for dislodging waste material and receiving the dislodged waste material from the colon for removal;

a first tube stowable in said carrier during transportation for coupling said lavage liquid pump to said speculum for delivery of lavage liquid thereto;

a second tube stowable in said carrier during transportation for coupling said speculum to said waste reservoir in said carrier to deliver dislodged waste from the colon to said waste reservoir;

a pressure regulator tower adapted to be disassembled and stowed in said carrier during transportation, said pressure regulator tower housing a regulator valve coupled to said first tube for maintaining the pressure of lavage liquid delivered to said speculum below a predetermined threshold;

first and second sphincter valves stowable in said carrier during transportation, said first sphincter valve being couplable in line with said first tube for selectively opening and closing communication therethrough to pulse the delivery of lavage liquid to the colon and said second sphincter valve being couplable in line with said second tube for selectively opening and closing communication through said second tube; and control means stowable in said carrier during transportation, said control means being couplable to said lavage liquid pump, to said first sphincter valve, and to said second sphincter valve and being programmed to actuate said pump and said valves according to a predetermined cycled schedule to deliver lavage liquid to and drain dislodged waste from the colon according to a predetermined cycled schedule to clear the waste from the colon.

25. The apparatus of claim 24 and wherein said carrier comprises a cloth bag formed with compartments for containing the functional elements of the apparatus during transportation.

26. The apparatus of claim 25 and wherein said lavage liquid reservoir and said waste reservoir comprise plastic bags.

27. The apparatus of claim 26 and wherein said pump housing is formed with an upwardly open port adapted to receive lavage liquid to fill the lavage liquid reservoir prior to use of the apparatus.

28. The apparatus of claim 27 and further comprising a tube coupling said regulator valve to said upwardly open port for directing overflow lavage liquid from said regulator valve back to said lavage liquid reservoir.

29. The apparatus of claim 28 and wherein said first and second sphincter valves are each unitarily molded from a substantially flexible rubberized material.

30. The apparatus of claim 29 and wherein said first and second sphincter valves are molded of a silicone rubber material.

31. The apparatus of claim 30 and wherein said first and second sphincter valves are coupled in line with their respective tubes at locations closely adjacent to said speculum to minimize lavage liquid waste and to enhance the cycled pulsed operation of the apparatus.

32. A portable colonic lavage assembly comprising a lavage liquid reservoir, a waste liquid reservoir, a speculum, a pump, a first valve communicating with said pump, a second valve communicating with said waste liquid reservoir, a controller operably connected to said pump and said first and second valves, said controller programmed with a pulse schedule to effect delivery of pulsing lavage liquid to the colon at a predetermined rate, and a portable carrier configured to contain the functional elements of said colonic lavage assembly for transportation between one location and another to provide mobility to patients dependent upon periodic colonic lavages.

33. A method of delivering a colonic lavage comprising the steps of:

(a) providing a speculum adapted to be positioned in a colon, said speculum being adapted to deliver lavage liquid to the colon and to receive waste from the colon for disposal;

(b) providing a source of lavage liquid and a first conduit coupling the source to the speculum for delivering lavage liquid to the speculum under a regulated pressure less than a predetermined limit;

(c) providing a first sphincter valve in line with the first conduit for selectively opening up and closing off communication through the first conduit to pulse delivery of lavage liquid to the colon;

(d) providing a second conduit coupled to the speculum for receiving waste from the speculum and directing the waste to a remote location for disposal;

(e) providing a second sphincter valve in line with the second conduit for opening up and closing off communication through the second conduit;

(f) positioning the speculum in a colon; and (g) selectively opening and closing the first and second sphincter valves according to a predetermined timing schedule to deliver pulsed lavage liquid to the colon to dislodge waste therein and remove the dislodged waste to a remote location for disposal.

34. The method of claim 33 and where in step (b) the source of lavage liquid comprises a frame constructed of substantially hollow tubular elements connected together to form a substantially sealed interior cavity for containing the lavage liquid.

35. The method of claim 34 and wherein the frame is portable for being moved to a patient to receive a colonic lavage.

36. The method of claim 35 and wherein step (g) further comprises cycling the first and second sphincter valves by alternately opening the first sphincter valve while closing the second sphincter valve and closing the first sphincter valve while opening the second sphincter valve according to a predetermined timing schedule.

37. The method of claim 36 and wherein the predetermined timing schedules gradually decrease the rate at which the sphincter valves are cycled over a predetermined time interval.

38. The method of claim 35 and wherein step (g) includes closing both the first and second sphincter valves for a predetermined length of time after a predetermined amount of lavage liquid has been delivered to the colon to hold the lavage liquid in the colon for dislodging waste material therein.

39. The method of claim 33 and wherein step (b) includes coupling a gravity actuated ball valve to the first conduit to maintain the pressure at which lavage liquid is delivered to the speculum to a value less than a predetermined threshold.

40. A method of delivering a colonic lavage comprising the steps of:

(a) providing a speculum adapted to be positioned in a colon, said speculum being adapted to deliver lavage liquid to the colon and to receive waste from the colon for disposal;

(b) providing a source of lavage liquid and a first conduit coupling the source to the speculum for delivering lavage liquid to the speculum under a regulated pressure less than a predetermined limit;

(c) providing a first sphincter valve in line with the first conduit for selectively opening up and closing off communication through the first conduit to pulse delivery of lavage liquid to the colon;

(d) providing a second conduit coupled to the speculum for receiving waste from the speculum and directing the waste to a remote location for disposal;

(e) providing a second sphincter valve in line with the second conduit for opening up and closing off communication through the second conduit;

(f) positioning the speculum in a colon; and (g) selectively opening and closing the first and second sphincter valves according to a predetermined timing schedule to deliver pulsed lavage liquid to the colon to dislodge waste therein and remove the dislodged waste to a remote location for disposal, including the step of closing both the first and second sphincter valves for a predetermined length of time after a predetermined amount of lavage liquid has been delivered to the colon to hold the lavage liquid in the colon.

41. The method of claim 40, and where in step (b) the source of lavage liquid comprises a frame constructed of substantially hollow tubular elements connected together to form a substantially sealed interior cavity for containing the lavage liquid.

42. The method of claim 41 and wherein the frame is portable for being moved to a patient to receive a colonic lavage.

* * * * *